United States Patent [19]  
Bücheler et al.

[11] 4,446,127  
[45] May 1, 1984

[54] PROCESS FOR THE PREPARATION OF PHARMACEUTICAL AND COSMETIC DISPERSIONS

[75] Inventors: Manfred Bücheler, Overath; Bernd Klinksiek, Bergisch-Gladbach; Hans Gehringer, Cologne; Hildegard Schnöring, Wuppertal, all of Fed. Rep. of Germany

[73] Assignee: Bayer Aktiengesellschaft, Leverkusen, Fed. Rep. of Germany

[21] Appl. No.: 422,336

[22] Filed: Sep. 23, 1982

Related U.S. Application Data

[63] Continuation of Ser. No. 280,615, Jul. 6, 1981, abandoned.

[30] Foreign Application Priority Data

Jul. 24, 1980 [DE] Fed. Rep. of Germany ....... 3028005

[51] Int. Cl.³ .............................................. A61K 7/42
[52] U.S. Cl. ..................................................... 424/59
[58] Field of Search .................................. 424/59, 302

[56] References Cited

U.S. PATENT DOCUMENTS 4,002,733  1/1977  Degen et al. .......................... 424/59
4,364,930  12/1982  Griant et al. ......................... 424/59

FOREIGN PATENT DOCUMENTS 0629433  10/1961  Canada ................................. 424/59

*Primary Examiner*—Delbert R. Phillips
*Assistant Examiner*—F. T. Moezie
*Attorney, Agent, or Firm*—Sprung, Horn, Kramer & Woods

[57] ABSTRACT

The invention relates to a process for preparing fine-particled, stable, pharmaceutical or cosmetic dispersions which comprises dispersing the entire inner phase in 5–40% by volume of outer phase, then adding the remainder of the outer phase, all under predetermined conditions.

3 Claims, 2 Drawing Figures

4,446,127

PROCESS FOR THE PREPARATION OF PHARMACEUTICAL AND COSMETIC DISPERSIONS

This is a continuation of application Ser. No. 280,615, filed July 6, 1981 abandoned.

BACKGROUND OF THE INVENTION

The invention relates to a process for the preparation of a fine-particled, stable, pharmaceutical or cosmetic dispersion consisting of an aqueous phase and an organic phase which is insoluble or not completely soluble in water.

Pharmaceutical and cosmetic emulsions are usually prepared by a procedure in which the fatty phase, or organic phase, which has been melted at temperatures of 60° to 70° C., and the entire aqueous phase, which has been brought to the same temperature, are combined, and pre-emulsified, in a stirred kettle and the crude emulsion thus obtained is cooled to 20° to 40° C. in a jacket cooler or flow-through cooler and then very finely dispersed with a high-pressure homogeniser.

The disadvantage of this process is that the entire batch must first be heated and, after pre-emulsification, must necessarily be cooled again in order then to bring the entire emulsion, which frequently has only a small amount of disperse fatty phase, to the desired fineness by means of high-pressure homogenizers. Such an energy-intensive temperature program is necessary, since when the surface are of the disperse phase is increased by the homogenization, the stability of the emulsion at elevated temperature and with simultaneous exposure to mechanical stress is insufficient. Enforced stability to heat and shearing stresses by emulsifiers is not permitted, since the amount and nature of the emulsifier system are to be selected according to pharmacological view points and from the point of view of the storage stability of the end product, and not according to the far higher stability requirements during production.

The invention is based on the object of developing a process for the preparation of pharmaceutical and cosmetic emulsions, which have a more favorable energy balance, whilst giving the same yield.

SUMMARY OF THE INVENTION

According to the present invention there is provided a process for the preparation of a fine-particled, stable, pharmaceutical or cosmetic dispersion consisting of an aqueous phase and an organic phase which is insoluble or not completely soluble in water, in which the entire inner phase is dispersed to a particle size of 0.1 to 10 $\mu$m in only 5 to 40% by volume of the outer phase for the intended finished dispersion at a temperature above the liquefaction point of the organic phase and of the aqueous phase, preferably at a temperature between 40° and 180° C., and the dispersion is then diluted, without changing the particle size, with the remaining 60 to 95% by volume of the outer phase, the temperature of which is below the solidification point of the inner phase.

The "inner phase" is also called the "disperse phase" and the "outer phase" is also called the "continuous phase". In cosmetic dispersions, the outer (continuous) phase is generally the aqueous phase and the inner (disperse) phase is generally the fatty phase.

The process according to the invention is thus based on a procedure in which emulsion concentrates with a very high content of disperse phase are prepared at elevated temperatures and the particle size distribution, once achieved, is frozen by introducing the emulsion concentrate into the cold remainder of the aqueous phase. Surprisingly, it has been found that the fineness of these emulsion concentrates is better than, or at least as good as, the fineness of the low-concentration emulsions prepared by customary processes. This contradicts certain learned opinions that the fineness which can be achieved would decrease as the volume concentration of disperse phase increases (see for example A. Mersmann and H. Grossmann: Dispergieren im flüssigen Zweiphasensystem (Dispersing in a Liquid Two-phase System), in Verfahrenstechnische Fortschritte beim Mischen, Dispergieren und bei der Wärmeübertragung in Flüssigkeiten (Technological Advances in Mixing and Dispersing and in Heat Transfer in Liquids), Preprints, GVC in VDI, Düsseldorf, December 1978, pages 141/155).

In many cases, it is advantageous for the temperature and the volume ratio of the two phases to be adjusted such that a reversal of phases takes place during dispersion. If, in the process described above, for example, 5 to 40% of the aqueous phase is introduced into the entire fatty phase and is dispersed, the aqueous phase initially forms the inner (disperse) phase in the outer (continuous) fatty phase. During dispersion, a reversal of the phases then takes place, as a function of the temperature and volume ratio of the two phases, to the effect that the aqueous phase is converted into the outer phase and the fatty phase is converted into the inner phase. The phase reversal temperature associated with a certain volume ratio can easily be determined empirically without problems. It is, of course, also possible to prepare water-in-oil formulations with the aid of the phase reversal process.

In one preferred embodiment, one or more substances which are sensitive to heat and shearing are added, if appropriate as a separately prepared emulsion, during dilution with the remaining outer phase.

In another preferred embodiment the aqueous phase consists of an aqueous solution of glycerol, or glycol ether (preferably ethylene glycol), ethylene glycol monomethyl or monoethyl ether or the corresponding propylene glycol compounds, a $C_1$ to $C_6$ monohydric alcohol (preferably an alkanol), a cosmetic compound or a pharmaceutically active compound, with the addition of one or more additives which increase the viscosity and one or more preservatives, and the organic phase, which is insoluble or not completely soluble in water, consists of a mixture of glycerol ester (preferably glycerol carboxylic acid ester, such as glycerol $C_1$–$C_4$-alkane carboxylic acid ester) or fatty acid ester and/or liquid or semisolid or solid hydrocarbon(s), with a polyhydric alcohol (especially a di- or tri-hydric $C_1$–$C_3$-alkanol), of non-ionic emulsifier and a fat-soluble pharmaceutical or cosmetic active compound.

In the finished end product, the organic phase is in general the inner phase and the aqueous phase is the outer phase.

The process of the present invention has the following advantages.

1. A high space/time yield coupled with a favorable heat balance is achieved with the new process. This is particularly true for dispersions with a low content of disperse phase (inner phase), because only 5 to 40% of the continuous phase (outer phase) participates in the actual emulsifying operation. The dilution with the cold outer phase, which corresponds to the last process step, simultaneously ensures cooling of the emulsion. Special heat exchangers (coolers) can be dispensed with. In practice, for a given installation, the improved yield leads either to shorter cycle times or 2 to 5 times the amount of end product, if the capacity of the diluting kettle is correspondingly increased.

2. The process also has the advantage that additives which are sensitive to shearing and heat are not damaged if they are first added in the last step, during dilution with the cold outer phase. In this stage, the emulsion is no longer exposed to thermal and mechanical stresses.

3. If the process is carried out such that a reversal of phases takes place during dispersion, so that the organic phase becomes the inner phase, the shearing stresses on the product during dispersion can be kept small. In this manner, colloidal structures and high-molecular constituents of the organic phase are destroyed to a lesser extent.

The process according to the invention can be carried out either continuously or discontinuously (charge process).

BRIEF DESCRIPTION OF THE DRAWINGS

The process technology will now be illustrated with reference to the accompanying drawings in which.

DETAILED DESCRIPTION OF THE INVENTION

Figure 1:
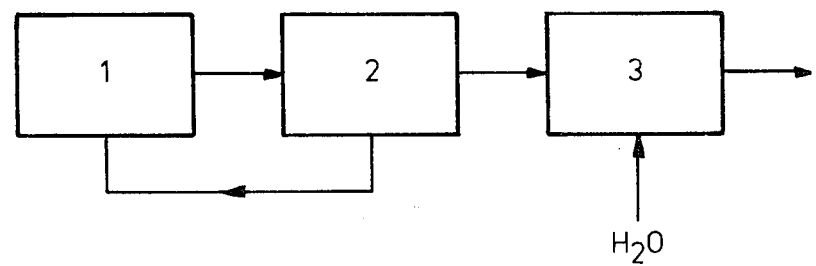
FIG. 1 shows schematically one embodiment of the charge process.

According to FIG. 1, the organic phase is sucked or pumped from a stock kettle 1 into a dispersing machine 2 together with 5 to 40% by volume of the aqueous phase, and is emulsified to the desired particle size at temperatures of 55° to 60° C., and the emulsion is recirculated into the stock kettle 1. The throughput amounts and circulation amounts are adjusted via rotameters and valves. After dispersion, the emulsion concentrate is transferred to the diluting kettle 3, which contains most of the aqueous phase, at a temperature of 20° C. A homogenous end product is as a rule obtained without further stirring.

Figure 2:
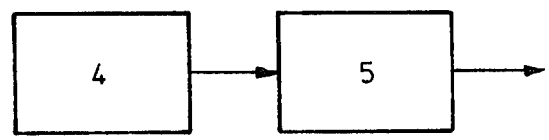
FIG. 2 shows schematically another embodiment of the charge process.

In the variant according to FIG. 2, dispersion is carried out in a stirred kettle 4, which is simultaneously the batch kettle. After dispersion and homogenization, the emulsion concentrate is drained off into a storage tank 5, which contains the cold aqueous phase. A homogeneous end product is likewise formed.

Dispersion is carried out by known processes and with customary emulsifying machines, such as by continuous direct emulsification, in which regulated streams of the phases to be emulsified are fed continuously to an emulsifying machine and are homogenized, or by initially introducing the aqueous phase into a kettle, emulsifying the organic phase therein and then homogenizing the mixture, or by initially introducing the organic phase into a kettle, emulsifying the aqueous phase therein, reversing the phases and then homogenizing the mixture.

Customary emulsifying machines are, for example, high-pressure homogenizers, ultrasonic homogenisers and jet homogenizers, as well as rotor/stator dispersing machines.

The particle size during dispersion can be determined by optical microscopy or solely with the aid of ultrasonic absorption and/or light-scattering spectroscopy.

The process according to the present invention will now be illustrated by the following Examples.

EXAMPLE 1

(Process embodiment of FIG. 1)

Using a dispersing machine which operates by the rotor/stator principle, the organic phase (fatty phase), consisting of 100 to 180 kg of oleic acid decyl ester, 0.5 to 2 kg of antifoaming agent, 0.1 to 0.2 kg of antioxidants and 20 to 80 kg of emulsifier, which was cetyl-stearyl alcohol or sodium cetyl-stearyl sulphate+nonionic emulsifiers, and the aqueous phase, consisting of 100 to 300 kg of water, 10 to 60 kg of UV filter substance, which was novantisol acid with added sodium chloride, and 0.5 to 1.5 kg of preservatives were sucked in, emulsified and recirculated into a batch kettle. The throughput amounts and circulating amounts were in each case adjusted to about 350 kg/hour via rotameters and valves. The emulsion temperature was 50° to 65° C. After all of the organic phase (fatty phase) had been transferred to the batch kettle, 20 to 40 kg of perfume oil were also stirred into the emulsion concentrate and the emulsion concentrate was then forced into 1,000 to 1,200 kg of diluting water at 20° C. in a diluting kettle at a throughput of about 2,000 kg/hour by means of a dispersing machine. A sunlight-protection milk with a high degree of dispersion was formed.

EXAMPLE 2

(Process embodiment of FIG. 2)

The fatty phase (organic phase), consisting of 2 to 4 kg of oleic acid decyl ester, 2 to 5 kg of isopropyl myristate, 3 to 6 kg of paraffin oil, 0.5 to 1.1 kg of polyoxyethylene stearate and 0.5 to 1.2 kg of sorbitane-fatty acid ester, was initially introduced, at a temperature of 60° C., into an ointment-making kettle provided with a cage stirrer, and 7 to 15 kg of the aqueous phase, consisting of 15 kg of non-neutralized carboxyvinyl polymer solution and 0.2 to 0.8 kg of paraffin oil, at 20° C., were added thereto. From the initial water-in-fat emulsion, a fat-in-water emulsion was formed by stirring and homogenizing by means of the cage stirrer. A reversal of the phases thus took place in this process, that is to say the aqueous phase which was initially present as the outer phase became the inner phase during dispersion.

After a homogenization time of 15 minutes at 40° C., the emulsion concentrate had reached the desired degree of dispersion and was drained off into a stirred storage tank, into which 40 to 60 kg of water 0.1 to 0.5 kg of alantoin and 20 to 30 kg of non-neutralized carboxyvinyl polymer solution (=a total of 0.3 to 0.8 kg of "Carbopol" in the formulation) had been initially introduced, and was neutralised with 0.2 to 0.6 kg of neutralizing agent, which was triethanolamine or sodium hydroxide solution. The homogeneous end product was a cosmetic emulsion.

What is claimed is:

1. A process for the preparation of a fine-particled, stable, pharmaceutical or cosmetic dispersion consisting of an aqueous phase and an organic phase which is insoluble or not completely soluble in water, which comprises dispersing the entire inner phase at a temperature between 40° and 180° C. to a particle size of 0.1 to 10 μm in only 5 to 40% by volume of the outer phase for the desired finished dispersion at a temperature above the liquefaction point of the inorganic phase and of the aqueous phase, and then diluting the resulting dispersion without changing the particle size, with the remaining 60 to 95% of the outer phase, the temperature of which is below the solidification point of the inner phase, the temperature and volume ratio of said two phases being adjusted so that a reversal of phases takes place during dispersion.

2. A process according to claim 1, in which substances which are sensitive to heat and shearing are added, as a separately prepared emulsion, during dilution with the remaining outer phase.

3. A process according to any of claims 1 or 2, in which the organic phase consists of a mixture of glycerol ester or fatty acid ester and/or liquid, semisolid or solid hydrocarbon(s) with a polyhydric alcohol, a non-ionic emulsifier and a fat-soluble pharmaceutical or cosmetic active compound, and the aqueous phase consists of an aqueous solution of glycerol, a glycol, a $C_1$ to $C_6$ monohydric alcohol, a cosmetic compound or a pharmaceutically active compound, with the addition of one or more substances which increase the viscosity and one or more preservatives.

* * * * *